(12) United States Patent
Morazzoni et al.

(10) Patent No.: US 7,323,441 B2
(45) Date of Patent: Jan. 29, 2008

(54) USE OF LUPIN CONGLUTIN FOR THE TREATMENT OF TYPE II DIABETES

(75) Inventors: Paolo Morazzoni, Milan (IT); Marcello Duranti, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/545,103

(22) PCT Filed: Feb. 6, 2004

(86) PCT No.: PCT/EP2004/001111

§ 371 (c)(1),
(2), (4) Date: Aug. 10, 2005

(87) PCT Pub. No.: WO2004/071521

PCT Pub. Date: Aug. 26, 2004

(65) Prior Publication Data

US 2006/0142185 A1    Jun. 29, 2006

(30) Foreign Application Priority Data

Feb. 11, 2003   (IT)   .......................... MI2003A0237

(51) Int. Cl.
   *A61K 38/00*   (2006.01)
   *C07K 14/00*   (2006.01)
(52) U.S. Cl. .......................... 514/2; 530/350
(58) Field of Classification Search ................ 530/350; 514/12; 435/7.1
   See application file for complete search history.

(56) References Cited

OTHER PUBLICATIONS

AAC49787, 131 aa, linear PLN Sep. 26, 2002, conglutin alpha [*Lupinus angustifolius*], pp. 1-2.*
AAB31199 ,31 aa, linear PLN Nov. 8, 1994 conglutin gamma heavy subunit, LalbC gamma heavy subunit, p. 1.*
Q96474, 81 aa, linear PLN Feb. 7, 2006, Albumin 1 precursor (A1) Contains: Albumin 1 chain b (A1b), pp. 1-2.*
Duranti et al., Thermal stabilities of lupin seed conglutin gamma protomers and tetramers, J Agric Food Chem. Apr. 2000, vol. 48, No. 4, pp. 1118-11123.*
Scarafoni A. et al., Cloning, sequencing and expression in the seeds and radicles of two Lupinus albus conglutin gamma genes, Biochim Biophys Acta. May 2001, pp. vol. 1519, No. 1-2 pp. 147-151.*
Pereira, Frederico C. et al: "Insulinotropic action of white lupine seeds (Lupinus albus L.): effects on ion fluxes and insulin secretion from isolated pancreatic islets" Biomedical Research, 22(2), 103-109 Coden: Bresd5; ISSN: 0388-6107, 2001, XP009033243 *p. 104, Preparation of lupine extracts* P. 108, col. 1, para 2-p.108, col. 2, para* abstract.
Woldemichael G M et al.: "Tripertene glycosides of *Lupinus angustifolius*" Phytochemistry, Pergamon Press, GB, vol. 60, No. 4, Jun. 2002, pp. 323-327, XP004354728 ISSN: 0031-9422 *p. 323, Introduction *.
Database Chemabs 'Online! Chemical Abstracts Service, Columbus, Ohio, US; Villarroel, Mario et al: "Chemical, sensory and clinical characterization of lupine marmalades" XP002287708 retrieved from STN Database accession No. 127: 345533 cited in the application abstract.
Waesche A et al: "New processing of lupin protein isolates and functional properties." Nahrung 45 (6) 393-395 2001Cess Eng., Fraunhofer-Inst. for Process Eng. & Packaging, Giggenhauserstr. 35, D-85354 Freising, Germany. E-Mail Wae(A)Ivv.Fhg.De, 2001, XP009033277 *p. 393, Materials and methods* abstract.
Sirtori C R et al: "Proteins of White Lupin Seed, a Naturally Isoflavone-Poor Legume, Reduce Cholesterolemia in Rats and Increase LDL Receptor Activity in HepG2 Cells" Journal of Nutrition 2004 United States , vol. 134, No. 1, 2004, pp. 18-23, XP001182166 ISSN: 0022-3166 table 4 & Archivos Latinoamericanos de Nutricion, 46 (3), 234-237 Coden: Alanbh; ISSN: 0004-0622, 1996.
Komatsu S et al: "Plant basic 7 S globulin-like proteins have insulin and insulin-like growth factor binding activity." Febs Letters, Dec. 9, 1991, vol. 294, No. 3, Dec. 9, 1991, pp. 210-212, XP002287707 ISSN: 0014-5793 * p. 210, Introduction, last paragraph * * Fig. 1 *.

* cited by examiner

*Primary Examiner*—Robert Mondesi
(74) *Attorney, Agent, or Firm*—Young & Thompson

(57) ABSTRACT

A method for the use of lupin conglutin gamma or of proteins showing homology higher than 50% with lupin conglutin gamma, for the preparation of a medicament, food supplements or foods for the treatment of type II diabetes, pharmaceutical and nutritional compositions containing lupin conglutin gamma, and the use of lupin conglutin gamma as therapeutical agent, in particular as hypoglycemizing agent. Lupin conglutin gamma may be used in pure form or in form of extracts, mixtures or concentrates.

4 Claims, 3 Drawing Sheets

USE OF LUPIN CONGLUTIN FOR THE TREATMENT OF TYPE II DIABETES

FIELD OF THE INVENTION

The present invention relates to the use of lupin conglutin for the treatment of type II diabetes.

TECHNICAL BACKGROUND

Lupin (*Lupinus albus*), an annual plant belonging to the class of Leguminosae, has been grown since ancient times in the Mediterranean area and in Middle East for its seeds which are used both for alimentary purposes (due to their remarkable protein contents) and in traditional medicine as anthelmintic and antiparasitic agents.

Lupin seeds contain toxic quinolizidine ring alkaloids, such as lupanin, 13-oxy-lupanin, multiflorin and derivatives, and methyl-albin, which are known to exert depressing and paralyzing actions on Central Nervous System. Said alkaloids, which are responsible for the bitter taste of lupin seeds, and occur in large amounts in wild lupin seeds, but in poor amounts in the so-called sweet lupin (*Lupinus albus*), can be removed by maceration in water.

The prevalent protein fraction in lupin seeds is the globulin one, which accounts for 87% of the total. Said fraction consists of water-insoluble proteins, which are soluble in diluted saline solutions (Duranti et al. Phytochemistry, 20, 2071-2075, 1981). Conglutin gamma accounts for about 6% of the total globulins. The protein apparent molecular weight, as determined by gel-filtration, is approx. 199,000 Da (Duranti et al. in: Lectins: Biology, Biochemistry, Clinical-Biochemistry-Vol. 11 (Van Driesche E, Rougè P, Beeckams S, Bog-Hansen T C eds.) 1997, Textop Publ., Hellerup, Denmark, pp. 881-85, 1997). Conglutin gamma consists of a monomer of apparent molecular weight of 47.000 Da. The reduction of the monomer shows that it consists of two polypeptide chains, with apparent molecular weight of 30.000 Da and 17.000 Da, respectively, linked by a disulfide bridge (Restani et al. Phytochemistry, 20, 2077-2083, 1981).

A tetrameric structure has been suggested for lupin conglutin gamma based on the molecular mass values obtained under native and denaturant conditions. Conglutin gamma light subunit lacks covalently bonded carbohydrates, while the heavy subunit has been found to be glycosylated.

The amino acids composition significantly differs from most lupin spare proteins (Restani et al. 1981, supra). Conglutin gamma contains, in fact, a number of sulfated amino acids and a fair amount of lysine, threonine and trypthophan, and proves very resistant to proteolysis by both endogenous and exogenous proteases (Duranti, Narhung, 30, 271-274, 1986).

The knowledge of the amino acid sequence of the protein (Scarafoni et al., Biochim. Biophys. Acta 1519, 147-151, 2001) allows to exclude any sequence homology with spare proteins, catalytic or structural proteins, also from other sources. Conglutin gamma shows homologies with or similarities to other proteins, such as soy BG7S (70% homology) (Kagawa et al., Febs Letters, 226, 145-149, 1987; Komatsu et al., Biosci. Biotech. Biochem. 58, 1705-1706, 1994) and with EDGP, a glycoprotein from carrot seed (58% homology) (Satoh et al., Planta, 188, 432-438, 1992), whose function has yet to be clarified.

The use of lupin total extract as hypoglycemia was described by Horvath (*J. Pharmacol.* (Amer.), 38, 303, 1930), which proposed it as a substitute for insulin in mild to medium diabetes mellitus. Subsequently, Clementi and Torrisi (*Boll. Soc. It. Biol. Sper.*, 9, 1004, 1935 e *Arch. Fisiol.*, 34, 290, 1935) identified the hypoglycemizing active ingredient in the alkaloid lupanin, whose effect was however transient.

The hypoglycemizing effect of lupin meal was described also recently in Mario Villaroel et al, Archivos Latinoamericanos de Nutrición, Vol. 46, N. 3, 1996, pp. 234-237), which suggest the use of plums jam containing lupin meal for use as dietetic food for diabetics.

As far as conglutin gamma is concerned, Duranti et al., (Phytochem. 56(6), 529-533, 2001) described its ability to interact with different metals. At pH neutral, conglutin gamma has the highest affinity for $Zn^{2+}$ ion. Moreover, conglutin gamma is bonded in an affinity chromatography column complexed with $Zn^{2+}$ and $Ni^{2+}$; the bonded protein can be eluted using buffering agents at pH below 6 or containing EDTA or imidazole. Conglutin gamma retention curves in metal affinity column are congruent with the titration curve of histidine side group (pKa=6).

However, the use of conglutin gamma for the treatment of type II diabetes has to date not been disclosed.

According to the present invention, it has been found that lupin conglutin gamma as well as proteins showing homology higher than 50% with lupin conglutin gamma, exert remarkable hypoglycemizing action.

Examples of known proteins showing homology higher than 50% with lupin conglutin gamma include soy BG7S (70% homology) (Kagawa et al., Febs Letters, 226, 145-149, 1987; Komatsu et al., Biosci. Biotech. Biochem. 58, 1705-1706, 1994) and EDGP (58% homology) (Satoh et al., Planta, 188, 432-438, 1992).

Conglutin gamma and homologues proteins also proved very powerful in reducing plasma curves after glucose administration in the rat.

SUMMARY OF THE INVENTION

Therefore, the present invention relates to the use of lupin conglutin gamma and of proteins showing homology higher than 50% with lupin conglutin gamma for the preparation of a medicament, food supplements or foods for the treatment of type II diabetes.

The present invention further relates to pharmaceutical or nutritional compositions comprising lupin conglutin gamma or proteins showing homology higher than 50% with lupin conglutin gamma, as active ingredient.

DETAILED DESCRIPTION OF THE INVENTION

Lupin conglutin gamma is preferred, either as a substantially pure protein or as a lupin protein mixture or extract containing said conglutin gamma. Substantially pure means a concentration typically higher than 80% by weight, preferably higher than 90%.

Figure 3:
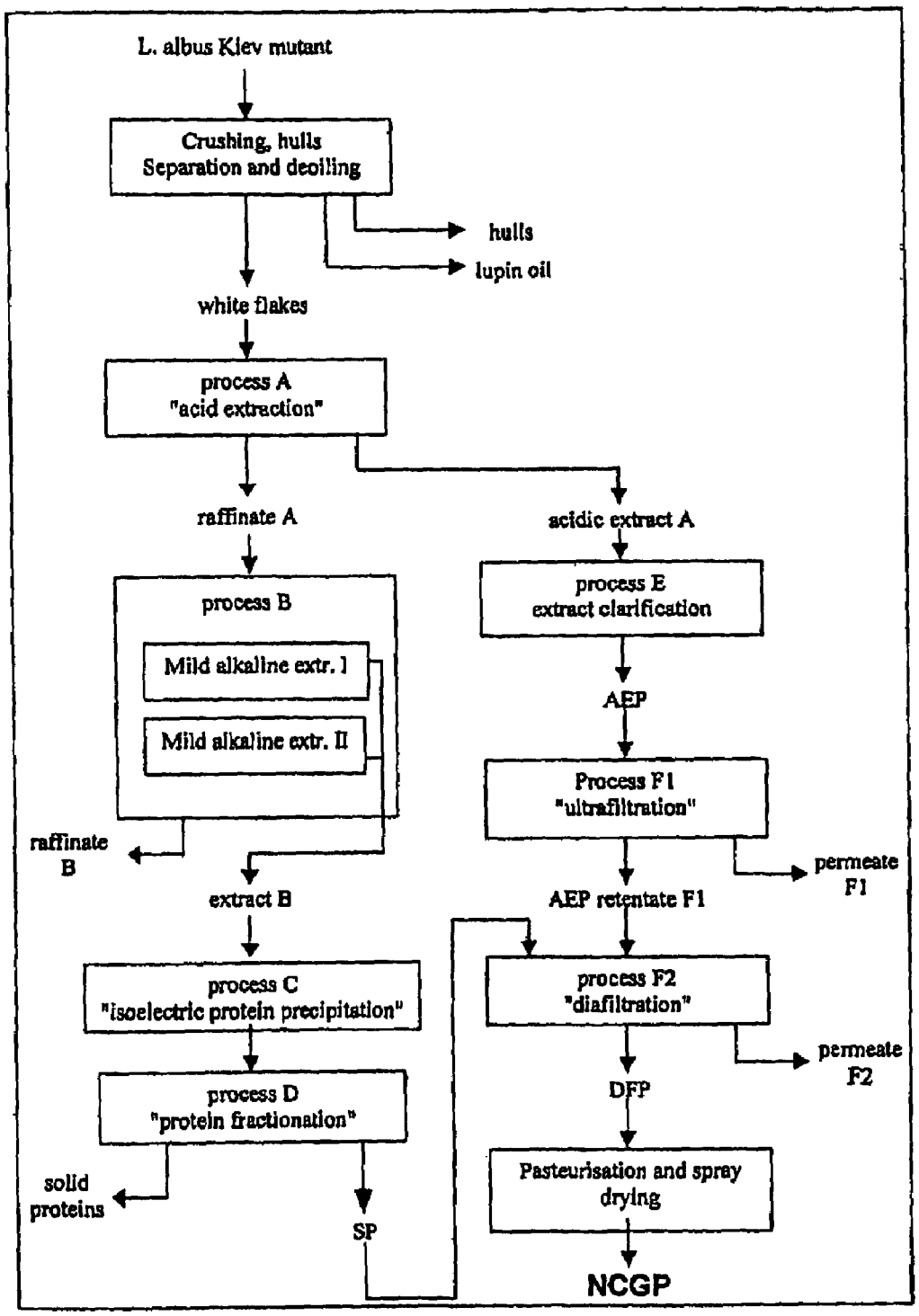
FIG. 3 shows a process for producing conglutin gamma.

Conglutin gamma can be obtained according to the process schematized in FIG. 3.

According to said process, lupins are crushed, kernels are dehulled and flaked, which are then deoiled by extraction with solvents. After that, deoiled flakes are subjected to an extraction process A under acidic conditions to obtain raffinate A and acidic extract A, which in turn are subjected to further treatments.

Starting from raffinate A, the following steps are carried out:
B) two subsequent extractions of raffinate A under slightly alkaline conditions, to obtain raffinate B, which is discarded, and extract B;
C) precipitation of the proteins from extract B by treatment with acids;
D) fractionation of the proteins, elimination of the solid proteins and clarification of the supernatant (SP) which is used at a later step.

At the same time, starting from acidic extract A resulting from the acid extraction process A, the following steps are carried out:
E) clarification of extract A to obtain clarified extract (AEP);
F1) ultra-filtration of AEP to obtain F1-retentate;
F2) diafiltration of the mixture resulting by combining SP and F1-retentate, to obtain retentate DFP and F2-permeate (which is discarded);
G) pasteurization and spray-drying of DFP to obtain NCGP (native conglutin gamma).

The results of the pharmacological experimentation carried out with conglutin gamma are reported in the following.

The hypoglycemizing activity of lupin conglutin gamma was tested in rats compared with metformin (reference standard).

EXAMPLE 1

Male CD strain rats, of the starting weight 275-300 g, were used. The animals were housed in makrolon cages in environment with automatic control of light (12 hour light/ 12 hour darkness cycles), temperature (21±1° C.) and humidity (60±5%).

Lupin conglutin gamma prepared as reported in Example 2 was used. 100 rats (divided into in 5 groups of 30 animals each) were pre-treated (time−30 min) with:
Group 1: carrier (1% carboxymethylcellulose [CMC]; 2 ml/kg os)
Group 2: lupin conglutin gamma (50 mg/kg os in 1% CMC)
Group 3: lupin conglutin gamma (100 mg/kg os in 1% CMC)
Group 4: lupin conglutin gamma (200 mg/kg os in 1% CMC)
Group 5: metformin (50 mg/kg os in 1% CMC)

All rats were subsequently treated (time 0 min) orally with glucose (2 g/kg) to increase glucose plasma levels.

Immediately before the glucose administration (time 0 min) and 30, 60 and 90 min after the glucose administration, all the animals (n=5 rats for each time) were anaesthetized with sodium thiopental (50 mg/kg i.p.) and 5 ml of blood was drawn from the vena cava. Blood samples were collected in syringes containing EDTA (7.5 mM) as anticoagulant, and immediately subjected to centrifugation (2000 g×10 min at 4° C.) to obtain the plasma necessary for the enzymatic quantitation of glucose.

The quantitation of the glucose in rat plasma was carried out in triplicate by enzymatic assay (absorbance at 505 nm) and the glucose concentration was expressed in mg/dl.

More precisely, an enzymatic kit (Glucose-Trinder from Sigma Aldrich, cat. 315-500) containing all the reagents necessary for the Trinder reaction (glucose-oxidase method) was used.

Furthermore, both the spectrophotometer calibration and the reading quality on the different plasma samples were validated by standard reagents from Sigma-Aldrich (Calibrator, cat. A-2539; ACCUTROL Normal, cat. A-2034; ACCUTROL Abnormal, cat. A-3034). Lupin conglutin gamma of Example 2 was used. Metformin, carboxymethyl cellulose and the various kits for glucose quantitation, for quality control and for calibrating the apparatus were purchased from Sigma-Aldrich (Milan, Italy).

All the values reported in the tables are expressed as mean±mean standard error (M.S.E). Statistical analysis between Group 1 carrier-treated rats) and Groups 2, 3, 4 and 5 (animals treated with lupin conglutin gamma at different concentrations or with metformin) was carried out on the areas under the curve values (FIG. 2), first by variance analysis (one way) and subsequently by the Dunnett's test (two tails) with multiple comparison. Differences were considerate significant when P<0.05.

Results

Figure 1:
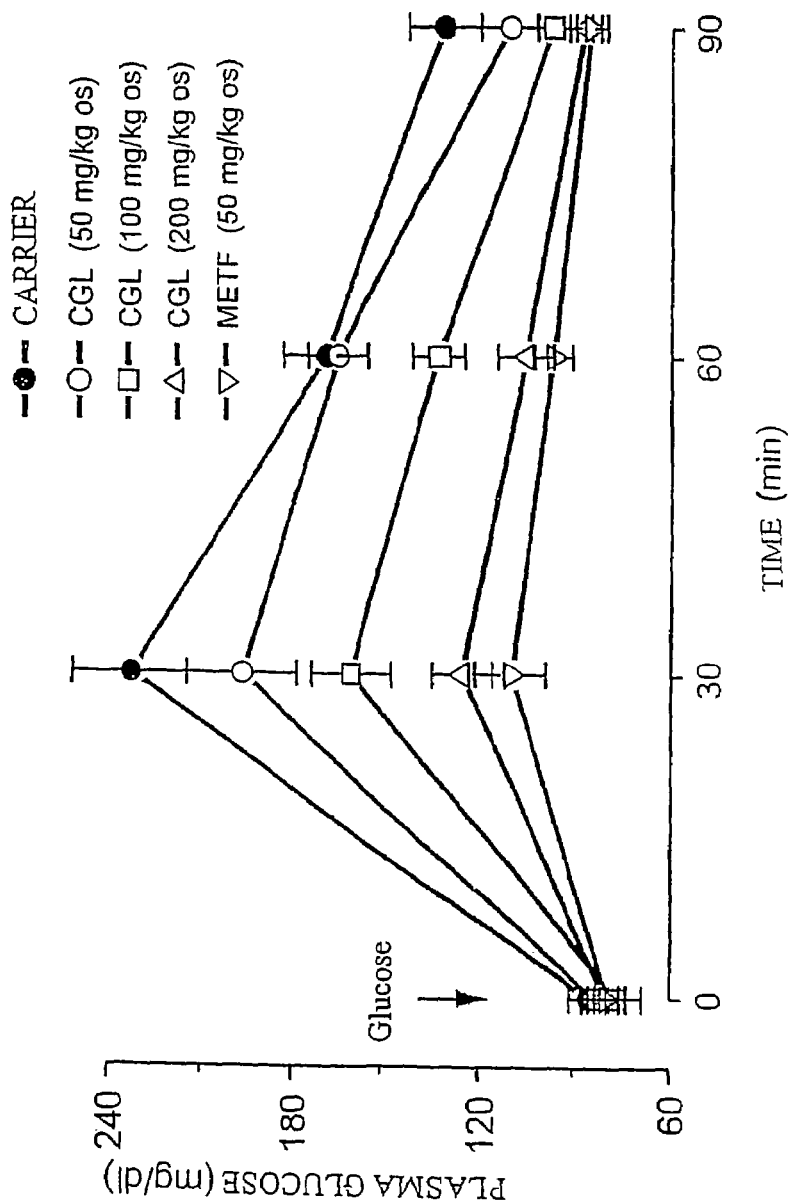
FIG. 1 shows the hypoglycemizing activity of lupin conglutin gamma (CGL) and metformin (METE) in rats. Each dot represents the mean±MSE of five rats.
Figure 2:
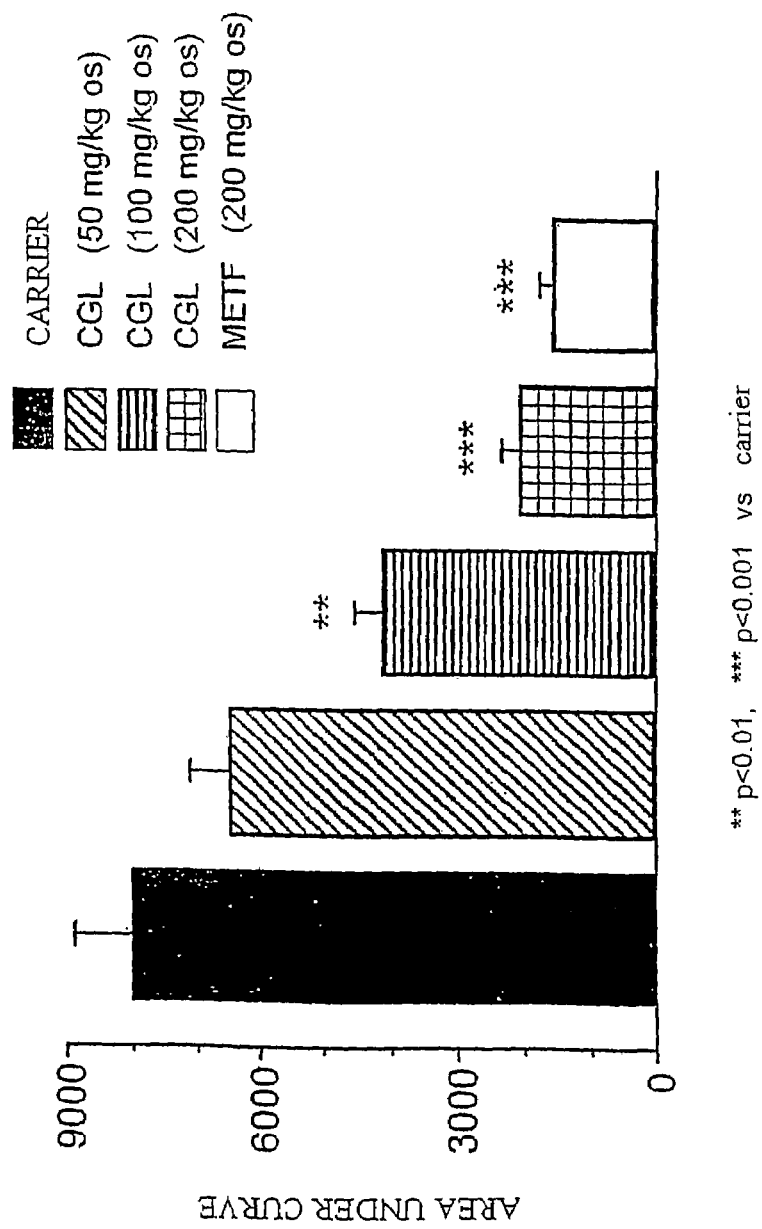
FIG. 2 shows the hypoglycemizing activity of lupin conglutin gamma (CGL) and metformin (METF) in rats. Areas under the curve (0 to 90 mm) concerning FIG. 1.

FIGS. 1 and 2 summarize the results of the experimentation.

The oral administration of 2 g/kg of glucose increased glucose plasma levels by 2.7 times (85±6 at 232±18 mg/dl; P<0.001) in control rats (carrier). Said increase reached its peak 30 min after glucose administration, then it gradually decreased in a time of 90 min (FIG. 1).

Pre-treatment rats with the lupin conglutin gamma, administered 30 min before the glucose at doses of 50, 100 and 200 mg/kg os, induced a significant, dose-dependent reduction the increase in glucose plasma levels (FIGS. 1 and 2).

More particularly, considering the area under the curve (AUC) values reported in FIG. 2, the effect obtained with 200 mg/kg os of lupin conglutin gamma (AUC=2090±238) was comparable to and not significantly different from that observed in Group 5 (animals pre-treated with 50 mg/kg os of metformin) (AUC=1565±201).

The obtained results clearly show that pre-treatment of rats with lupin conglutin gamma significantly reduces the increase in glucose plasma levels resulting from oral administration of glucose 2 g/kg.

EXAMPLE 2

Preparation of Lupin Flakes

Approximately 4.500 kg of lupins were crushed and hulls were separated from kernels, thus obtaining 3.440 kg of kernels and 1.060 kg of hulls. Crushed kernels were flaked in a roller mill, whose rolls were kept at a temperature below 40° C. to prevent protein denaturation. Yellow disk-shaped flakes were obtained, having bulk density of 300 to 330 kg/m$^3$.

Oil Extraction

Batches of 500 kg of flakes from step a) were filled up to 2 m height in a vertical pipe of 900 mm diameter and deoiled by percolation with hexane. The extraction procedure was repeated 4 times and consisted of:
1) percolation of white hexane until 500 l of mixture had been recovered in the tank,
2) recirculation of the mixture for 15 min,
3) drain off of the liquid portion for 15 min in steps 1 to 3 and for 30 min in the final extraction step.

Hexane still present in deoiled flakes was removed under vacuum (250 mbars) with stirring for 150 min, to the hexane final content was 250 ppm, which was subsequently reduced to 50 ppm though air blowing. Approx. 430 kg of white flakes was obtained.

A) Protein Extraction Under Acidic Conditions.

185 kg of white flakes were suspended in 1.800 ml of cold acidic water at pH 4.5-4.8 and at a temperature from 13.5 to 15.2° C., with mechanical stirring adjusted to 55 rpm, and extracted for 1 hour. Approximately 23.6 l of 3M HCl were used to keep pH acidic throughout the extraction. 385 kg of raffinate A and 1.600 l of acidic extract A were obtained by centrifugation.

B) Separation of the Protein Extract from the Raffinate Under Slightly Alkaline Conditions In a first step, 385 kg of raffinate A were extracted with 900 l of water at pH 7.2-7.4 and at 28.2 to 31.5° C., with mechanical stirring at 60 rpm, for 1 hour. The solution was added with 50 ml of anti-foaming agent Struktol SB 2010. Approximately 19.6 l of 3M NaOH were used to keep pH alkaline throughout the extraction.

Approximately 945 l of protein extract were separated from the raffinate by centrifugation.

In a second step, the raffinate obtained by centrifugation was extracted with 540 l of water at pH 7.3-7.4 and at a temperature of 29.0 to 32.0° C. for 15 min. 0.3 l of 3M NaOH were used to keep pH alkaline throughout the extraction. Approx. 595 l of protein extract II and 242 kg of raffinate B were obtained.

Protein extracts I and II were combined to obtain 1.450 l of protein extract B.

C) Precipitation of Proteins from the Protein Extract Under Acidic Conditions

Protein extract B (1.540 l) was added with 16 l of 3M HCl to adjust pH to 4.6-4.5 and with 50 ml of the above anti-foaming agent, with mechanical stirring at 85 rpm. Proteins precipitated at the iso-electric point (pH 4.5).

D) Separation of Precipitated Proteins from the Supernatant

The protein dispersion from step C) (approx. 1.550 l) having solids content ranging from 11.0 to 11.5 vol %, was separated with a disc-type separator at 6.830 rpm. Solids content in the resulting clarified extract was 0.0 to 0.1 vol %. Approximately 1.330 l of clarified supernatant (SP) and 213 l of sludge were separated. The dry matter content of the clarified supernatant was 0.4-0.5% and dry matter contained 70% total proteins.

E) Clarification of Acidic Extract A

Acidic extract A (1.600 l) from the acidic extraction A, having dry matter content ranging from 2 to 2.5 vol %, was clarified using a disc-type separator at 7.500 rpm. The solids content in the resulting clarified extract was from 0.1 to 0.15 vol %. Approx. 1.500 l of clarified extract (AEP) and 100 l of sludge were separated. The solids content in the clarified extract (AEP) was 2.2-2.5%, and dry matter contained 25% total proteins.

F1) Ultra-Filtration of Clarified Extract (AEP)

700 l of AEP were adjusted from pH 4.5 to pH 6.0-7.0 and concentrated through membrane ultra-filtration at 3 bars pressure and 40° C. until the final volume had been reduced by a factor of 10 compared with the starting volume.

The dry matter content of F1-retentate was approx. 7%, and dry matter contained 50% total proteins. F1-permeate was discarded.

F2) Diafiltration of SP and AEP 233 l of clarified supernatant (SP) from step D) were added step-by-step to F1-retentate, and the mixture was recirculated in the membrane until its volume had been reduced to that of the starting retentate. After the final dilution step, recirculation was continued until the dry matter content in the diafiltered retentate (DFP) had reached a maximum level, which ranged from 14.5 to 15.0%, and dry matter contained approx. 84% total proteins. F2-permeate was discarded.

G) Pasteurisation and Spray-Drying to Obtain NCGP

The diafiltered retentate (DFP) was adjusted from pH 6.5 to approx. pH 5.2, heated to 40-65° C. in a heat exchanger consisting of a jacketed pipe with 6 mm inner diameter and fed into a spray dryer. The air inlet temperature was adjusted to 195° C. and DFP feeding rate was 8 to 10 l per hour. The dry powder was separated from the air stream using a cyclone separator. The dry matter content ranged from 94.0 to 95.2%. Approximately 4.5 kg of native conglutin gamma (NCGP) was obtained from 40 l of DFP.

Conglutin gamma prepared according to this process contains 84.7% proteins, 0.6% oil and 6.4% dry matter. Dry matter contains a calculated amount of 8.3% nitrogen free substances (NFE). Nitrogen solubility index of NCGP at pH 7 in 1% aqueous solution is 72.5%.

According to the present invention, conglutin gamma will be administered orally, either alone or in combination with other substances with useful or complementary activity, formulated as tablets, capsules, granules, powders, syrups and the like. The pharmaceutical formulations can be prepared with conventional procedures, using ingredients known in the technique, such as excipients, ligands, disintegrants, lubricants, stabilizing agents, and the like. Dosage may vary, according to the symptoms, weight of the patient, severity of the disease and the like. In case of an adult human patient, the total daily dosage of lupin conglutin gamma will range from 150 to 750 mg, preferably from 50 to 250, in a single dose or in multiple doses, for example one to three times a day.

The invention claimed is:

1. A method for lowering plasma glucose levels in a subject comprising administering to said subject an effective amount of lupin conglutin gamma.

2. The method according to claim 1, wherein the lupin conglutin gamma is administered orally.

3. The method according to claim 1, wherein the lupin conglutin gamma is administered to said subject in a daily dosage of 150 to 750 mg per day.

4. The method according to claim 1, wherein the lupin conglutin gamma is administered in a form selected from the group consisting of tablets, capsules, granules, powder, and syrups.

* * * * *